United States Patent
Cohen

(10) Patent No.: US 9,535,083 B2
(45) Date of Patent: Jan. 3, 2017

(54) METHOD AND SYSTEM USING SAMPLE PROCESSING SYSTEM AND STORAGE UNITS

(71) Applicant: Beckman Coulter, Inc., Brea, CA (US)

(72) Inventor: Patrick Cohen, Deuil la Barre (FR)

(73) Assignee: Beckman Coulter, Inc., Brea, CA (US)

( * ) Notice: Subject to any disclaimer, the term of this patent is extended or adjusted under 35 U.S.C. 154(b) by 175 days.

(21) Appl. No.: 14/108,051

(22) Filed: Dec. 16, 2013

(65) Prior Publication Data

US 2014/0172154 A1   Jun. 19, 2014

Related U.S. Application Data

(60) Provisional application No. 61/738,260, filed on Dec. 17, 2012.

(51) Int. Cl.

| | | |
|---|---|---|
| G06F 7/00 | (2006.01) | |
| G01N 35/04 | (2006.01) | |
| B01L 3/00 | (2006.01) | |
| G01N 35/00 | (2006.01) | |

(52) U.S. Cl.
CPC ............. *G01N 35/04* (2013.01); *B01L 3/54* (2013.01); *B01L 3/5082* (2013.01); *B01L 3/5085* (2013.01); *B01L 2300/021* (2013.01); *G01N 2035/0096* (2013.01)

(58) Field of Classification Search
None
See application file for complete search history.

(56) References Cited

U.S. PATENT DOCUMENTS

| | | | |
|---|---|---|---|
| 2010/0028124 A1 | 2/2010 | Lackner et al. | |
| 2010/0049358 A1 | 2/2010 | Koch et al. | |
| 2010/0166605 A1* | 7/2010 | Hamada | G01N 35/02 422/65 |
| 2010/0303590 A1 | 12/2010 | Pedrazzini | |
| 2011/0065193 A1* | 3/2011 | Kitagawa | G01N 35/00613 436/43 |
| 2012/0283867 A1* | 11/2012 | Gelbman | G01N 35/04 700/215 |

* cited by examiner

*Primary Examiner* — Yolanda Cumbess
(74) *Attorney, Agent, or Firm* — Kilpatrick Townsend & Stockton LLP

(57) ABSTRACT

In some embodiments of the invention, the central controller may comprise a processor and a computer readable medium coupled to the processor. The computer readable medium comprises code, executable by the processor to implement a method. The method comprises identifying, by the processor, a sample container or a sample container holder associated with the sample container, and then accessing, by the processor, a location database storing mapping data correlating sample containers or sample container holders with sample containers to test regions in the storage unit. The test regions store sample containers with samples that have been or are to be tested according to different tests. After accessing the database, the method continues by providing, by the processor, a proposal for storage of the sample container or the sample container holder associated with the sample container in the storage unit.

20 Claims, 14 Drawing Sheets

METHOD AND SYSTEM USING SAMPLE PROCESSING SYSTEM AND STORAGE UNITS

CROSS-REFERENCES TO RELATED APPLICATIONS

This application is a non-provisional application of U.S. Provisional Patent Application No. 61/738,260, filed on Dec. 17, 2012, which is herein incorporated by reference in its entirety for all purposes.

BACKGROUND

Embodiments of the invention relate to sample container or sample container holder storage systems.

When sample tubes are conventionally processed by a sample processing system, samples may have to wait to be further processed or are held for retesting in some cases. In such cases, a technician may have to manually place the sample tubes containing the samples into storage units, such as a refrigerator for subsequent testing. There can be a number of reasons for this. For instance, a sample may need to be retested at a later date, so the sample may be stored for possible later use. In another example, an analyzer may not be ready or available to analyze a sample. Additionally, local country laws may require that certain types of samples be retained for defined periods of time for retesting, such as in France where it is required to maintain certain patient samples having infectious disease such as HIV or HCV for a defined period of time. The patient samples may then be stored in a storage unit such as a refrigerator for the defined period of time. When patient samples are stored, the technician will manually note the type of patient sample, i.e. HIV or HCV, the retention date and refrigerator location in a notebook (e.g., refrigerator 1, drawer 6). This allows the sample to be easily retrieved for further processing or disposal. The following are examples of these types of manual processes.

FIG. 1 shows a conventional process flow for processing samples in a serum bank using an automated sample processing system. In step 1000, sampled blood is placed into sample tubes. At steps 1002 and 1004, a pre-analytical process is performed using the automated sample processing system, and a sample aliquot is placed in a sample tube. In steps 1006 and 1008, the sample tube may be sorted and a bioassay may be performed. If a bioassay is not yet to be performed on a sample in a sample tube, then in step 1010, the sample tube may be positioned in a common box, uncorrelated with an analytical test code (e.g., one after another). In step 1012, a box reference such as the date may be associated with the box. Lastly, in step 1014, the box is stored in a freezer at a location selected by the technician who writes down the location of the sample and type of sample for future reference.

FIG. 2 shows another conventional process flow for a serum bank that is processed manually. In step 1020, blood is sampled and is placed into sample tubes. The samples in a sample tube may then be processed with bioassays in step 1022. Alternatively, in step 1024, the sample tube may be dedicated for a serum bank. The sample tube may be positioned in a common box uncorrelated with an analytical test code such as indicating that the patient sample is HIV or HCV positive (i.e., one after the other) in step 1026. In step 1028, the box number and positions of the sample tubes in the box are recorded in a laboratory book (step 1028). The box is then stored in a freezer (step 1030), and the position of the box in the freezer is recorded in the laboratory book (step 1032).

FIG. 3 shows another conventional process. In this process, blood samples may be placed in a number of sample tubes (step 1040). Some sample tubes may proceed along a post-analytical path and may be subject to a bioassay (step 1042). Other sample tubes may proceed along a pre-analytical path and may not be subject to the bioassay (step 1043). In step 1044, either post-analytical or pre-analytical samples may be aliquoted into new sample tubes or into a microtitre plate (step 1044). The tube or plate may be placed in a common box, uncorrelated with an analytical test code (i.e., random sample types) (step 1046), or may be positioned in a box that is dedicated to a single test such as Toxoplasmosis or Rubella or a single type of patient sample, e.g. HIV or HCV positive (step 1048). The box number and position of the tube or plate in the box are recorded in a laboratory book (step 1050), and the box is then placed into an open area of a freezer (step 1052). Again, the box may be placed in a random position of the freezer, or a specific area of the freezer can be defined for a specific type of patient sample, such as HIV or HCV. Again, certain countries, such as France, require the placement of like patient samples (HIV/HCV tested) in the same freezer location. The position of the box in the freezer is then recorded in the book (step 1054).

One system that addresses the above problem includes a software product called ItemTracker™ by ItemTracker Software Ltd. In this product, samples can be stored in a refrigerator and the locations of those samples can be tracked. However, the locations of the samples in the refrigerator correspond to different technicians that are responsible for processing the samples. Further, the software is essentially a stand-alone piece of software that is not integrated with any other instrument, thereby making it limited in its application.

Other systems that discuss storage are described in a number of U.S. Published patent applications. These are listed below.

U.S. Published Patent Application No. 20100028124 to Lackner et al. describes a laboratory storage and retrieval system that is used to store laboratory sample tubes and retrieve stored sample tubes. This published application describes a system that resorts sample tubes on the basis of the expiration dates of the contents of the sample tubes. According this published patent application, this simplifies the disposal of the expired samples.

U.S. Published Patent Application No. 2010/0049358 to Koch et al. discloses a method and system for handling sample tube racks. It discloses resorting sample tubes according to the diameters of the sample tubes and the sample tubes' shelf lives.

U.S. Published Patent Application No. 2012/0283867 to Gelbman et al. discloses an automated refrigerated specimen inventory management system. The system allows a user to identify desired pre- and post-analytical storage temperatures desired for each unique combination of sample/specimen type and test requested.

U.S. Published Patent Application No. 2010/0303590 to Pedrazzini discloses an apparatus for automatically depositing, preserving and retrieving biological material specimens in a refrigerated storage. Pedrazzini discloses a storage comprising a shelf counter consisting of a pair of optical fibers which detect the passage of a tab placed on the external wall of the shelves and an emitter-receiver pair adapted to detect the presence of a container during the handling between the storage and a bench.

Embodiments of the invention address these and other problems, individually and collectively.

BRIEF SUMMARY

In some of the conventional systems described above, storage of a sample in a sample container is performed manually without taking into account information received directly by an informatics system (information about specimen). However, in embodiments of the invention, a sample container and/or sample container holder can be automatically grouped according to information received by the laboratory information system. Embodiments of the invention also advantageously provide for complete traceability, from the initial identification of the samples (e.g., specimens) to the storage of these samples, without manual processing. This reduces the risk of error relative to the conventional systems.

One embodiment of the invention is directed to a method comprising identifying, by a processor, a sample container or a sample container holder associated with the sample container, and then accessing, by the processor, a location database storing mapping data correlating sample containers or sample container holders with sample containers to test regions in the storage unit. The test regions store sample containers with samples that have been or are to be tested according to different tests. The method also comprises after accessing the database, providing, by the processor, a proposal for storage of the sample container or the sample container holder associated with the sample container in the storage unit.

Another embodiment of the invention is directed to a central controller. The central controller may comprise a processor and a computer readable medium coupled to the processor. The computer readable medium comprises code, executable by the processor to implement a method. The method comprises identifying, by the processor, a sample container or a sample container holder associated with the sample container, and then accessing, by the processor, a location database storing mapping data correlating sample containers or sample container holders with sample containers to test regions in the storage unit. The test regions store sample containers with samples that have been or are to be tested according to different tests. After accessing the database, the method continues by providing, by the processor, a proposal for storage of the sample container or the sample container holder associated with the sample container in the storage unit.

Another embodiment of the invention is directed to a system comprising a central controller comprising a processor, and a computer readable medium coupled to the processor. The computer readable medium comprises code, executable by the processor to implement a method comprising: identifying, by a processor, a sample container or a sample container holder associated with the sample container; accessing, by the processor, a location database storing mapping data correlating sample containers or sample container holders with sample containers to test regions in the storage unit, wherein the test regions store sample containers with samples that have been or are to be tested according to different tests; and after accessing the database, providing, by the processor, a proposal for storage of the sample container or the sample container holder associated with the sample container in the storage unit. The system also comprises a sample container holder location database coupled to the central controller.

These and other embodiments of the invention are described in further detail below.

BRIEF DESCRIPTION OF THE FIGURES

FIGS. 9-13 shows additional graphical user interfaces according to embodiments of the invention.

DETAILED DESCRIPTION

Figure 1:
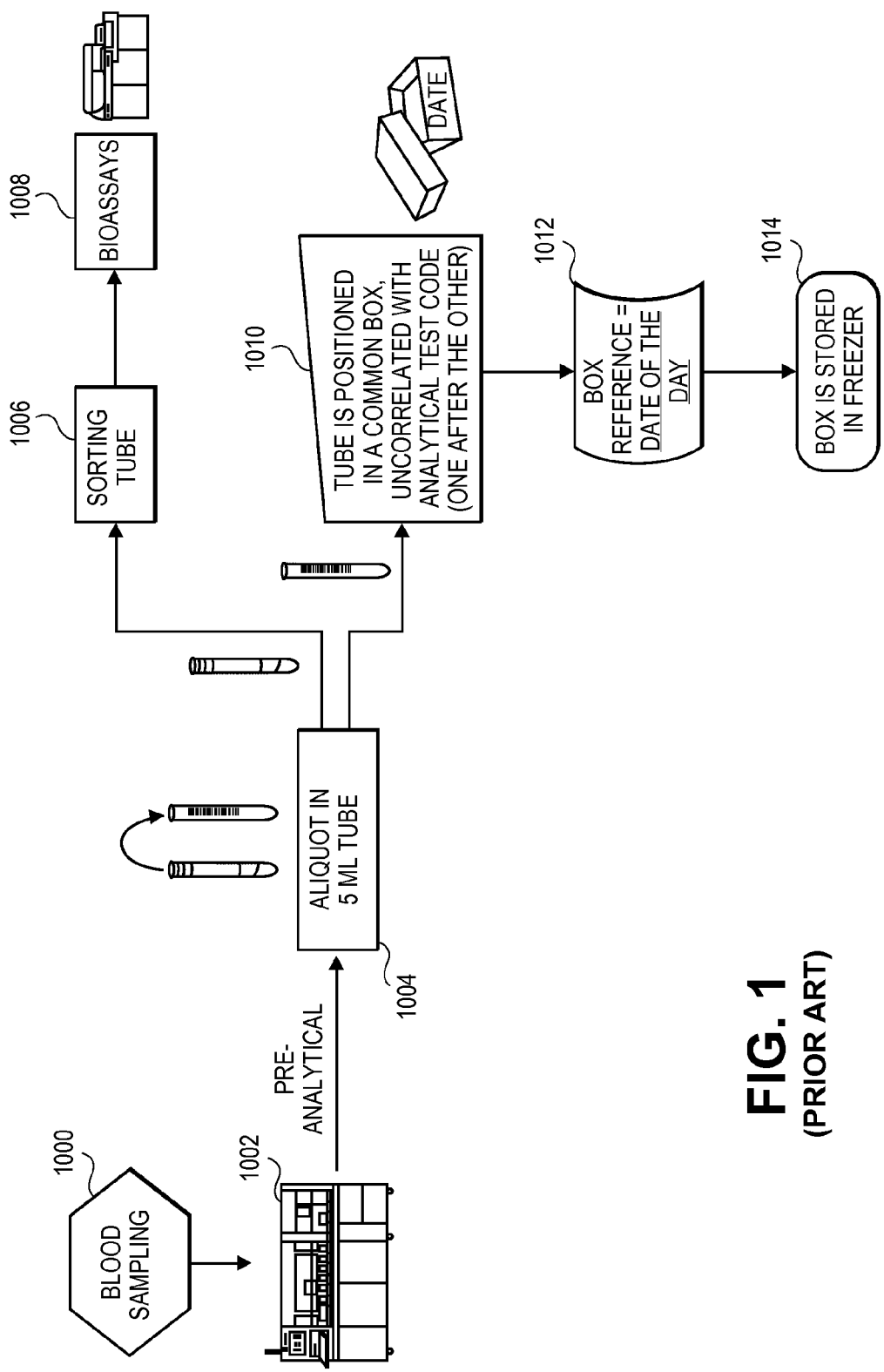
FIGS. 1-3 show diagrams illustrating conventional processes for storing sample tubes in freezers.
Figure 2:
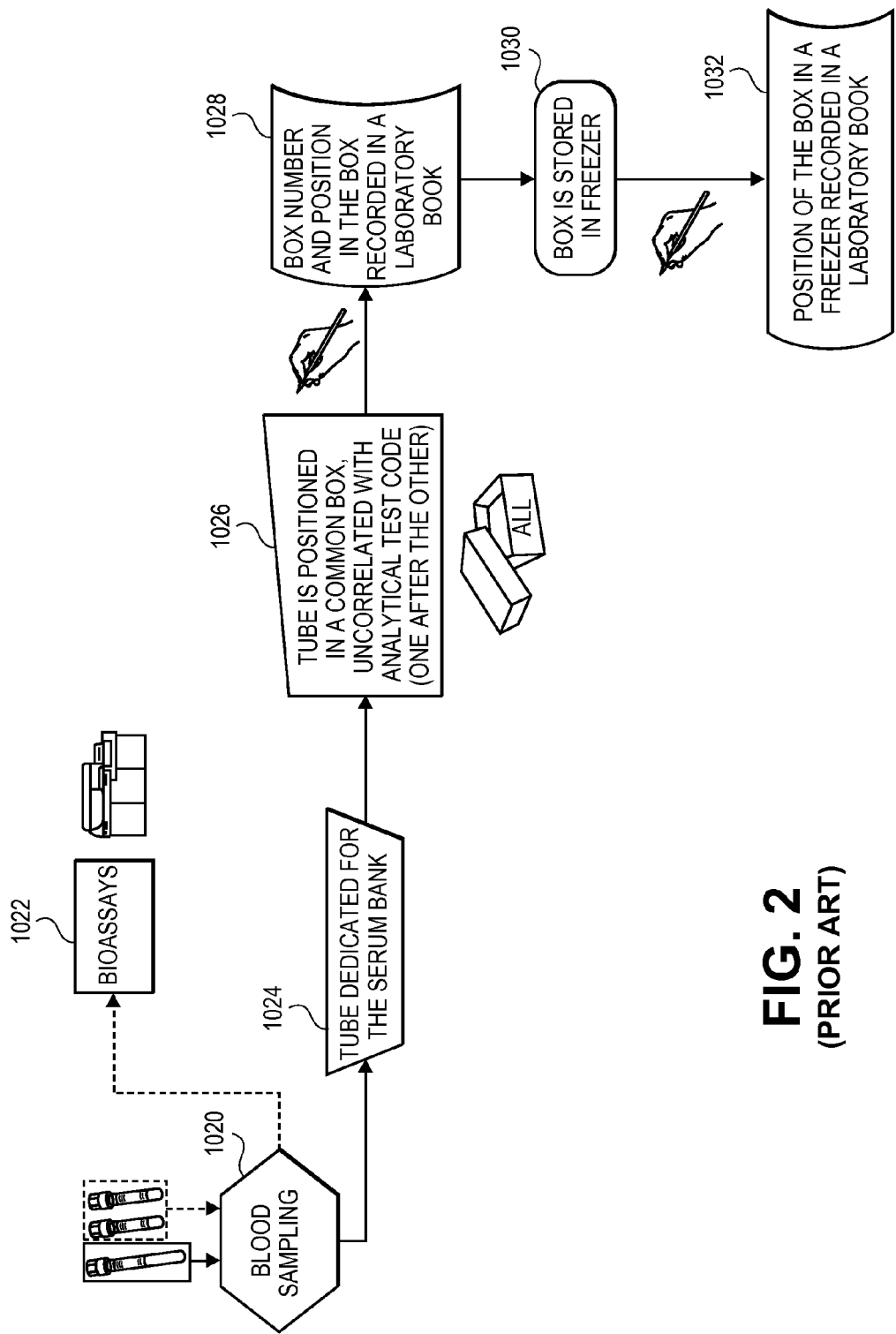
Figure 3:
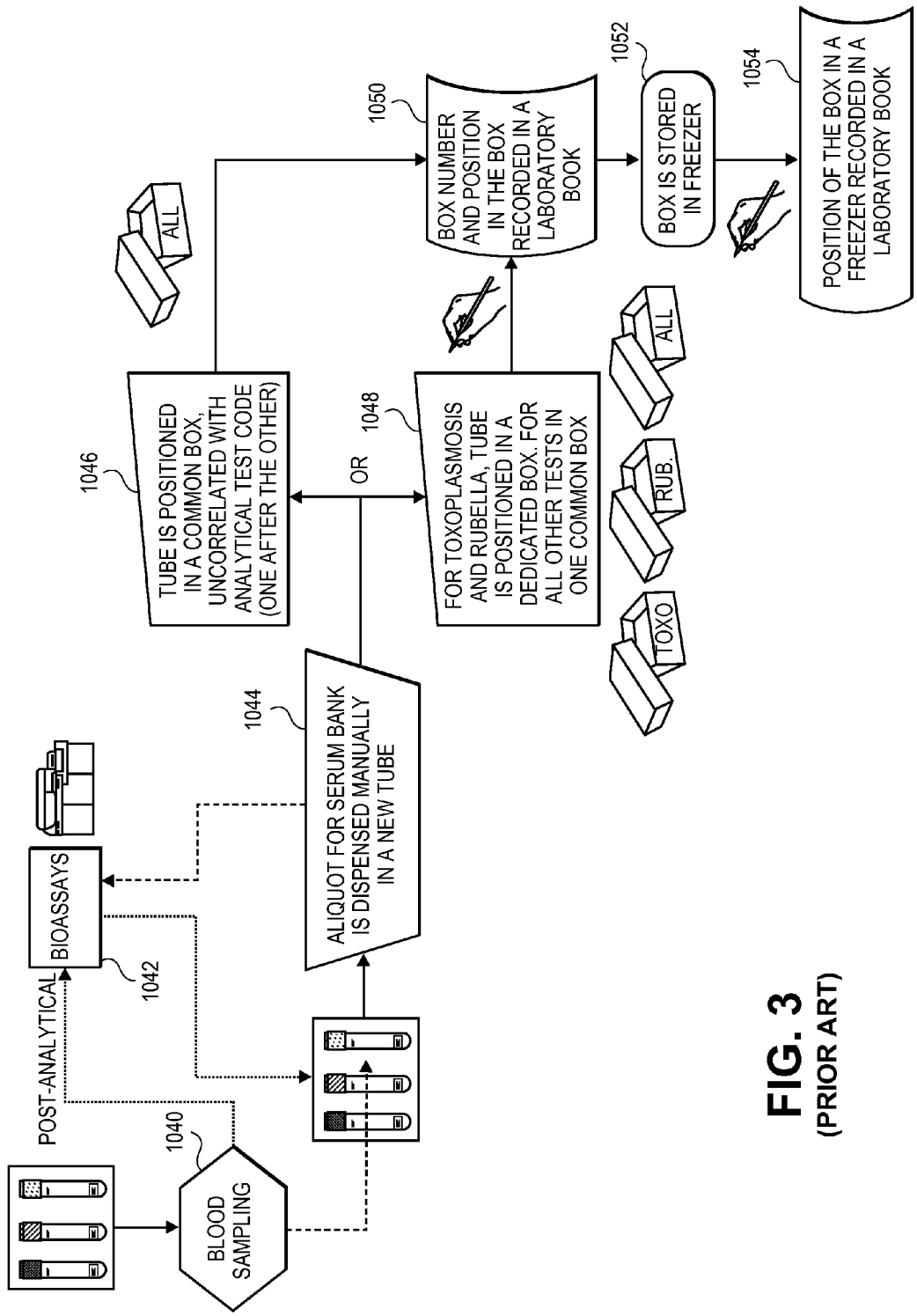

Embodiments of the invention provide for the traceability of a specimen during storage. Embodiments of the invention can work in combination with a sample processing system such as a laboratory automation system that can be already connected to a Laboratory Information System (LIS).

The LIS may store all specimen data (demographic data) in a database. Embodiments of the invention can utilize a user interface and an archiving system. Data of the specimen can be linked in the system with data associated with a 2D (two dimensional) multititer plate (e.g., via a 1D barcode, and/or 2D code of each microtube of the multititer plate) or other sample container (e.g., a sample tube).

In some embodiments, specimens can be dispensed in the 2D multititer plate. Algorithms implemented in system can propose the best storage unit and the best location within the best storage unit according to user definable settings. For example, a laboratory may have decided that all specimens for which there is a HIV test requested, will be stored in freezer 5, and drawer 1 of freezer 5.

In some cases, a single multiwall sample container may have samples that are subjected to different tests. In such cases, the system may determine that the test characteristic associated with the majority of specimens in a multititer plate. Using this information, the system may be used to determine how and where that sample container will be stored. For example, if the system determines that that 75% of specimens distributed in a 2D multititer plate had a request for HIV test, the system will suggest that the user store this 2D multititer plate in freezer 5, drawer 1. Freezer 5, drawer 1 may be associated with a location where HIV test samples are stored.

Embodiments of the invention also provide for patient information in a database. The database may be implemented with any suitable hardware and/or software. For example, it may include a scalable structured query language (SQL) database software program, such as that which is commercially available from Oracle™. In some embodiments, the database may be referred to as a Sorting-Drive SQL database.

The system according to embodiments of the invention provides a number of other advantages. These include the traceability of a specimen during storage, management of different user levels and groups, provision of a feature to adjust settings for different storage units, the monitoring of the availability of a storage unit, the provision of detailed storage instructions for each sample container (e.g., an MTP or a portion thereof), the provision of a search feature to search specimens retrieved, and the provision of a destocking feature to dispose of the specimen. The retrieval and destocking feature in the system includes security checks to ensure that the correct specimen is retrieved or destocked. Embodiments of the invention also provide a feature to destock specimens after a certain storage time (e.g., 1 year, 3 years, and from date to date).

Embodiments of the invention can be fully integrated and can provide for a high level of security. Differences between prior solutions include the use of 2D coding, minimum intervention by users, a decrease in the number of manual steps in the process, fewer errors, better traceability, minimal risk of errors during storage or retrieval of specimens, the ability to set up a serum bank in a pre-analytical phase, and the optimization of storage space in the storage units.

As noted above, in embodiments of the invention, storage units can be organized depending on the type of tests (patient analysis) that are performed on the samples. This can be advantageous, because the storage period deadlines for different samples can be different. Using embodiments of the invention, it is easy to retrieve or destock specimens according to the type of test to be performed on a sample. For example viral serology has a minimum 1 year storage (hepatitis viruses. HIV, rubella virus, cytomegalovirus, herpes virus, etc.) while prenatal diagnosis—infectious embryo fetopathic, has a minimum 3 years storage.

Prior to discussing specific embodiments of the invention, some descriptions of some terms may be helpful.

A "sample container" may be any suitable structure configured to hold a sample. It may have any suitable shape or form. In some embodiments, the sample container may be in the form of a sample tube, which may have an aspect ratio of greater than about 3:1. Such sample containers may be made of any suitable material including plastic, glass, etc. They may further include a sample tube body with a closed end and an open end, as well as a cap that is structured to cover and attach to the open end of the sample tube body. Another example of a sample container may be a plate with a number of wells (or a portion thereof) such as a microtiter plate.

In embodiments of the invention, a "sample container holder" may be in any suitable shape or form, and may comprise any suitable material. In some cases, the sample tube holder may be in the form of a sample tube rack. Sample container holders may include an array of recesses that can receive sample containers (e.g., sample tubes). They may also comprise any suitable material including plastic.

A "database" may include a collection of related data organized for convenient access. A database can operate on large quantities of information by inputting, storing, retrieving, and managing that information. A database uses a table format that is made up of rows and columns. Each piece of information is entered into a row, which then creates a record.

A "storage unit" may include any suitable unit for storing sample tubes and/or racks for storing sample tubes. An example of a storage unit may be a refrigerator or a cabinet. Storage units may include a number of drawers or shelves to hold sample containers or sample container holders. A storage unit may include a temperature controller to control the temperature inside of the storage unit.

Figure 4:
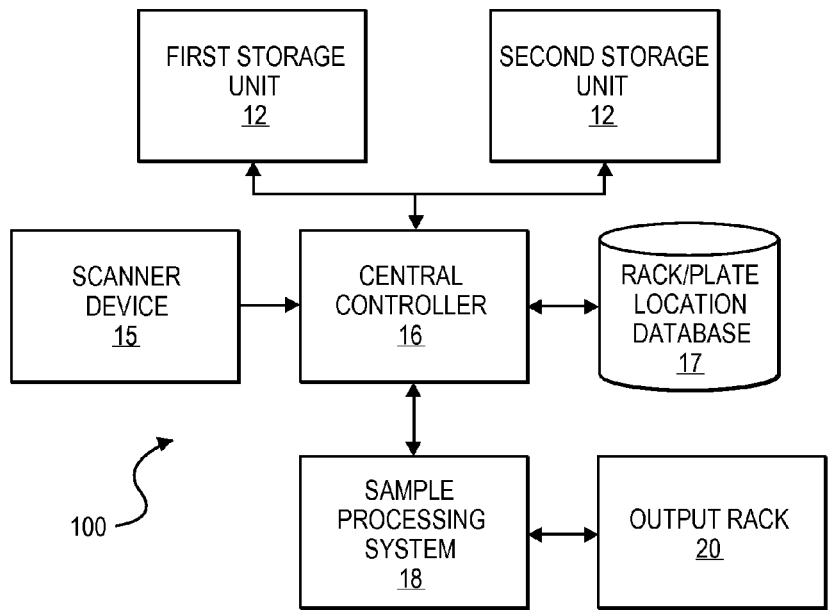
FIG. 4 shows a block diagram of a system according to an embodiment of the invention.

FIG. 4 shows a block diagram of a system 100 according to an embodiment of the invention. The system 100 comprises a first storage unit 12 and a second storage unit 14. The first and second storage units 12, 14 may be in communication with a central controller 16. The central controller 16 may in turn be in communication with a rack/plate location database 17, a scanner device 15, and a sample processing system 18. The sample processing system 18 may be associated with an output rack 20.

Although one sample processing system 18 and two storage units 12, 14 are coupled to and in communication with the central controller 16, it is understood that embodiments of the invention are not limited thereto. The systems according to embodiments of the invention may have any suitable number of sample processing systems and storage units. The storage units 12, 14 may also be of the same type or different types.

The sample processing system 18 may perform a number of different sample processing functions including, but not limited to centrifugation, sample loading, sample volume determination, decapping, and aliquotting. A suitable sample processing system may be an AutoMate™ 2500 sample processing system that is commercially available from Beckman Coulter. Inc., the assignee of the present application.

Once the sample processing system 18 processes samples in sample containers, they are placed in the output rack 20. The sample containers may be placed in the output rack 20 while they await processing by a downstream analyzer (not shown). If the downstream analyzer is not available or the sample in the sample container is not otherwise ready to be processed, then the sample container or the rack that is associated with the sample container may be placed in a storage unit such as the first and second storage units 12, 14. Additionally, and as the main benefit of an embodiment of the invention, once the samples have been subjected to analysis by a downstream analyzer it may be either a benefit or a requirement to retain the samples for future analysis. In accordance with this embodiment, the samples are subjected to storage in accordance with this embodiment of the invention for potential future retrieval and analysis. In some embodiments, the transfer of sample containers and/or sample container holders from the output rack to the first and second storage units 12, 14 may be manual, while in other embodiments, the transfer can be automatic (e.g., through a robot).

Figure 5:
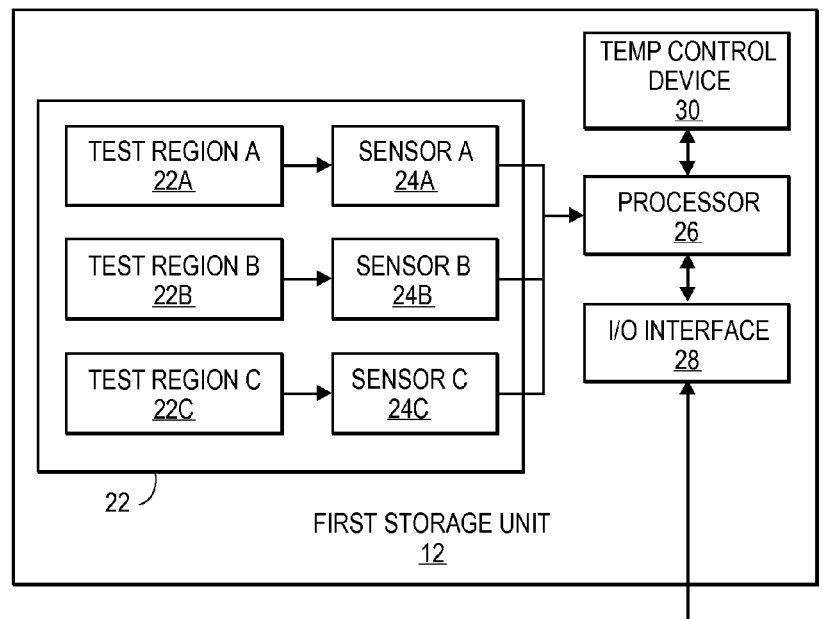
FIG. 5 shows a block diagram of a storage unit according to an embodiment of the invention.

FIG. 5 shows a block diagram of a first storage unit 12. The second storage unit 14 shown in FIG. 1 may have a similar or different configuration. FIG. 5 shows a storage area 22 for storing sample containers (e.g., sample tubes or microtiter plates) or sample container holders (e.g. racks for holding sample tubes). The storage area 22 may comprise a number of test regions 22A, 22B, 22C. The test regions 22A, 22B, 22C may store samples in sample containers that are intended to be tested by different testing methods. Each test region 22A, 22B, 22C may correspond to a drawer in a storage unit or a portion of a drawer or multiple drawers in a storage unit. Illustratively, the test regions 22A, 22B, 22C may respectively comprise samples that are to be tested for hepatitis, HIV, and rubella viruses. In another example, the different test regions could correspond to different immunoassay and/or chemical tests. Each test region 22A, 22B, 22C may include a number of locations which can hold sample containers or sample container holders.

In some embodiments, each test region may have one or more sensors 24A, 24B, 24C associated with it. Each sensor 24A, 24B, 24C may be configured to sense the presence or absence of a sample container or rack within the test region 22A, 22B, 22C. Suitable sensors may utilize any suitable optical, electrical or mechanical mechanism. In other embodiments, sensors 24A, 24B, 24C need not be present.

Any suitable sensor may be used in embodiments of the invention. Suitable sensors may include cameras, pressure sensors, optical emitter and detector combinations, RF ID sensors, etc.

In the embodiment shown in FIG. 5, the sensors 22A, 22B, 22C may be operatively coupled to a processor in the first storage unit 12, and the processor 26 may control the operation of the first storage unit 12 by controlling a temperature control device 30. The temperature control device 30 may provide temperature control including refrigeration and heating. For example, the temperature control device 30 may comprise a number of cooling coils, which can cool an internal environment of the first storage unit 12. The processor 26 may also control the communication between the central controller and the first storage unit 12 via an I/O (input/output) interface.

Figure 6:
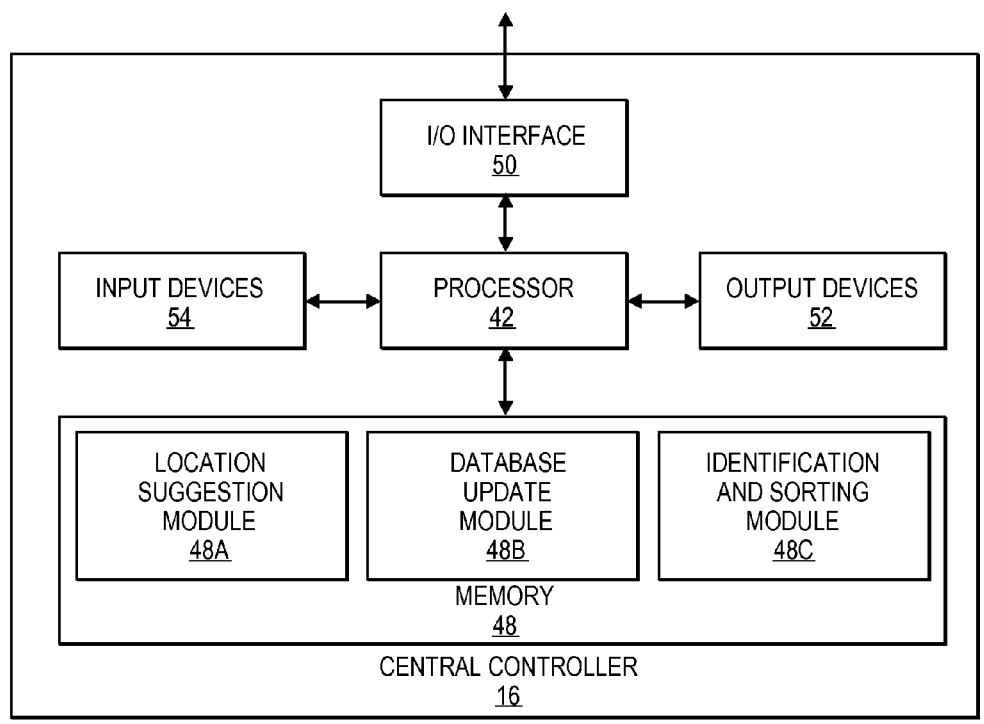
FIG. 6 shows a block diagram of a central controller according to an embodiment of the invention.

FIG. 6 shows a block diagram of a central controller 16 according to an embodiment of the invention. FIG. 6 shows a processor 42, which may be in communication with a memory 48, as well as a number of input devices (e.g., keyboard, mouse, etc.) 54, output devices (e.g., a display, speaker, etc.) 52, and in I/O interface 50. The memory 48 may store a location suggestion module 48A, a database update module 48B, and an identification module 48C.

The processor 42 may comprise any suitable type and/or number of data processing units. The processor 42 may comprise, for example, one or more commercially available microprocessors, which can operate together or separately to execute code on one or more computer readable media to cause the central controller 16 to perform certain functions.

The memory 48 may comprise any suitable combination of data storage devices, which contain computer readable media. For example, the memory 48 may comprise any combination of volatile and/or non-volatile memory such as, for example, buffer memory, RAM, DRAM, ROM, flash, or any other suitable memory device. The memory may further comprise an operating system, such as WINDOWS XP offered by Microsoft Corp., LINUX offered by various distributors, including Red Hat, Inc., or OS X offered by Apple Computer. It may store software for performing the steps in FIGS. 7A and 7B, which are described in further detail below.

The location suggestion module 48A comprises code, executable by a processor to case the central controller to suggest a location for a given sample container or rack for the sample container, after the identification module 48C identifies a given sample associated with a sample container or sample container holder. The suggested location could be determined based upon the type of test associated with a sample or samples in the sample container or sample container holder, the capacity of the different storage units, or vacancy of the storage units or areas within the storage units.

The database update module 48B can update the rack plate location database 17, by providing data to and retrieving data from the database 17. This module can update the database 17 when sample containers or their holders are placed into certain regions in a storage unit, or when the sample containers or their holders are removed from the storage units.

The identification and sorting module 48C may be used to identify sample containers or sample container holders by analyzing barcode data or other identification data associated with them. Records regarding samples associated with the sample containers or sample container holders can be stored in a sample identification database (not shown).

In some embodiments of the invention, the central controller may comprise a processor and a computer readable medium coupled to the processor. The computer readable medium comprises code, executable by the processor to implement a method. The method comprises identifying, by the processor, a sample container or a rack associated with the sample container, and then accessing, by the processor, a location database storing mapping data correlating sample containers or racks with sample containers to test regions in the storage unit. The test regions store sample containers with samples that have been or are to be tested according to different tests. After accessing the database, the method continues by providing, by the processor, a proposal for storage of the sample container or the rack associated with the sample container in the storage unit.

Figure 7A:
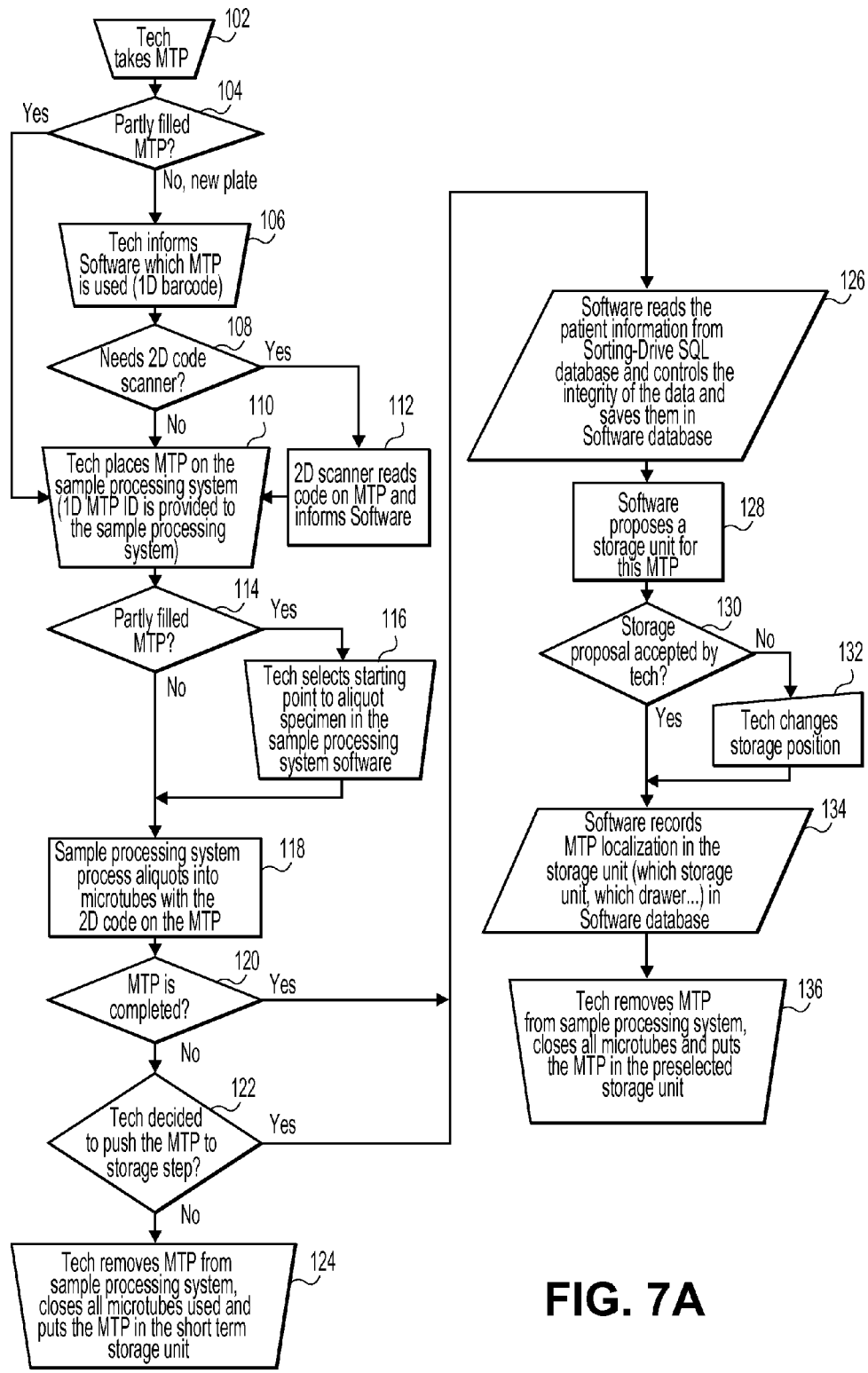
FIG. 7A shows a flowchart illustrating an archiving method according to an embodiment of the invention.

FIG. 7A shows a flowchart illustrating an archiving method according to an embodiment of the invention. The flowchart illustrates processing which can occur using a sample container in the form of a multititer plate. It is understood that the sample container can take other forms in other embodiments of the invention. Also, although some of the processing in this example occurs manually, in other embodiments, the processing may occur automatically. For instance, the transfer of a sample container such as a multititer plate to and from a storage unit may occur manually or automatically (e.g., with a robot) in embodiments of the invention. This also applies to FIG. 7B, which is described in further detail below as well.

In step 102, a technician can obtain a multititer plate. In other embodiments, the multititer plate may be a rack with a number of sample tubes.

In step 104, a determination is made as to whether or not the multititer plate is partially filled or not. If it is not filled, then the multititer plate can be considered new. Then, in step 106, the technician informs the central controller software as to which multititer plate is used. A barcode such as a one dimensional barcode may be scanned to identify the multititer plate. If the multitier plate is filled, then the process may proceed directly from step 104 to step 110 (which is described in further detail below).

In step 108, a determination is made as to whether a two-dimensional code scanner is needed, if the barcode identifying the multititer plate is a two-dimensional bar code. If a two-dimensional barcode is needed, than in step 112, a scanner reads the barcode on the multititer plate and informs the central controller software.

In step 110, the technician can then place the multititer plate in the sample processing system if the multititer plate is at least partially filled or if the multititer plate is appropriately identified.

In step 114, a determination is made as to whether the multititer plate is partially filled. If it is, then, using the central controller, the technician can select a starting point to aliquot a specimen (step 115). If it is not, then the sample processing system may process aliquots into microtubes in the microtiter plates with the two dimensional codes on the multititer plates (step 118). The central controller software can then identify the samples in the multititer plate by reading the barcodes associated with those samples.

In step 120, a determination is made as to whether the processing of the multititer plate is completed. If it is not, then the technician can decide to put the multititer plate into storage (step 122).

In step 124, if the technician decides not to put the multititer plate into storage, then the technician then removes the multititer plate from the sample processing system and closes all microtubes used and puts the multititer plate in a short term storage unit.

From steps 120 and 122, if the multititer plate is complete, data regarding those samples may be retrieved from the sample identification database, and this information may be saved into the rack/plate location database (e.g., database 17 in FIG. 1) (step 126). The central controller software can then determine which locations in which storage units may be appropriate to store the microtiter plate. Then, in step 128, the central controller software may propose a location for the multititer plate in a storage unit.

In step 130, a determination is made as to whether the storage proposal was accepted by the technician. If the proposal is not accepted, then a prompt is provided to request that the technician changes the storage position (step 132). If the proposal is accepted, then the central controller software records the multititer plate localization in the store unit (e.g., which storage unit, which drawer) in the database (step 134).

In step 136, the technician removes the multititer plate from the sample processing system, and closes all microtubes and puts the multititer plate into the pre-selected storage unit.

Figure 7B:
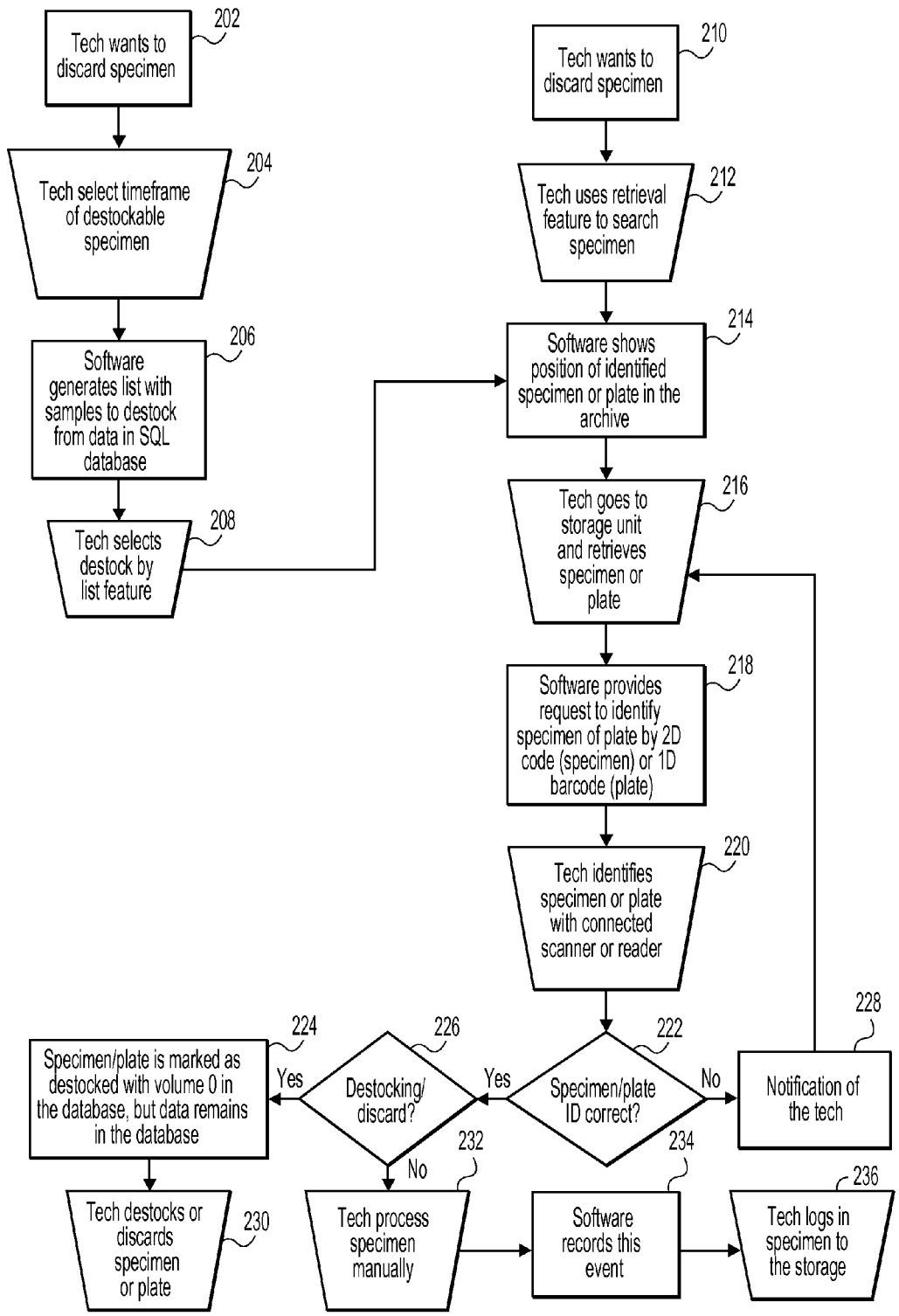
FIG. 7B shows a flowchart illustrating a destocking method according to an embodiment of the invention.

FIG. 7B shows a destocking flowchart according to another embodiment of the invention. The flowchart illustrates processing which can occur using a sample container in the form of a multititer plate. It is understood that the sample container can take other forms in other embodiments of the invention. Also, although some of the processing in this example occurs manually, in other embodiments, the processing may occur automatically. For instance, the transfer of a sample container such as a multititer plate to and from a storage unit may occur manually or automatically (e.g., with a robot) in embodiments of the invention.

In step 202, the technician determines that he wants to discard the sample (or specimen). The sample may be discarded because it is too old, or no more testing is needed.

In step 204, the technician selects a timeframe for the destockable specimen (step 204) and enters this information into the central controller software. For example, the technician may determine that he wants to discard samples in the storage units after a two week time period. Alternatively, the destocking time may correspond to the expiration dates of the specimens in the sample containers. Then, in step 206, the central controller software generates a list of samples to destock from data in the database (step 206).

In step 208, the technician selects a destock function by list feature, and then in step 214, the central controller shows the position of the identified sample (e.g., specimen), and sample container (e.g. a multititer plate) in the database.

Alternatively, in step 210, the technician decides that he wants to retrieve the sample for destocking. In step 212, the technician may use a retrieval feature in the central controller software to search for a specimen. In embodiments of the invention, a user may retrieve samples using any suitable information, including by name, primary code, patient ID an aliquoting date. Then, in step 214, the central controller software shows the position of the identified sample (e.g., specimen), sample container (e.g., a multititer plate) in the database.

In step 216, the technician goes to the storage unit to retrieve the specimen or plate. In step 218, the central controller software then provides a request to identify the specimen or plate with a connected scanner or reader. In step 220, the technician identifies the specimen or plate with the connected scanner or reader.

In step 222, a decision is made as to whether or not the specimen and plate ID are correct. If the specimen plate ID is not correct, then a notification is provided to the technician (step 228). If the specimen plate ID is correct, then a decision is made as to whether the plate is to be destocked or discarded (step 226). If the plate is discarded, then the specimen/plate is marked as destocked with the database is updated according (step 224). The location previously occupied by the plate is not indicated as being vacant in the database. The technician then destocks or discards the specimen or plate (step 230).

If the plate is not discarded, then the technician can process the specimen manually (step 232). The central controller software can then record this event (step 232) and the technician can log the specimen into the storage unit (step 236).

Figure 8:
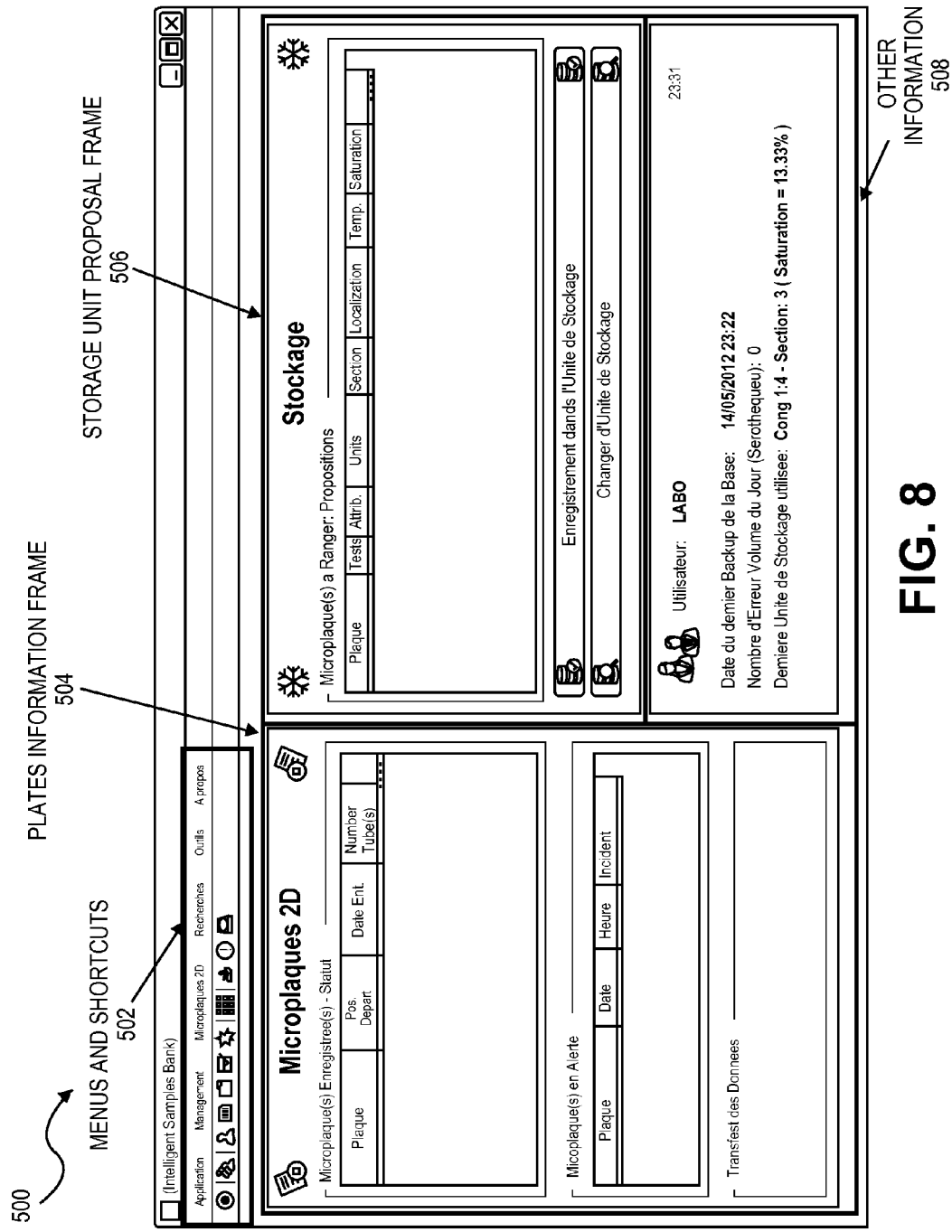
FIG. 8 shows a graphical user interface with a storage unit proposal frame.

FIG. 8 shows a graphical user interface 500 that can be used in embodiments of the invention. FIG. 8 shows a bar with menus and shortcuts 502, a plate information frame 404, and a storage unit proposal frame 506. The plate information frame 504 may provide information about a rack and/or sample tube, while the storage unit proposal frame 506 may provide information about proposed locations within the storage unit where a sample tube and/or rack may be stored. Another frame 508 for other information is also present.

Figure 9:
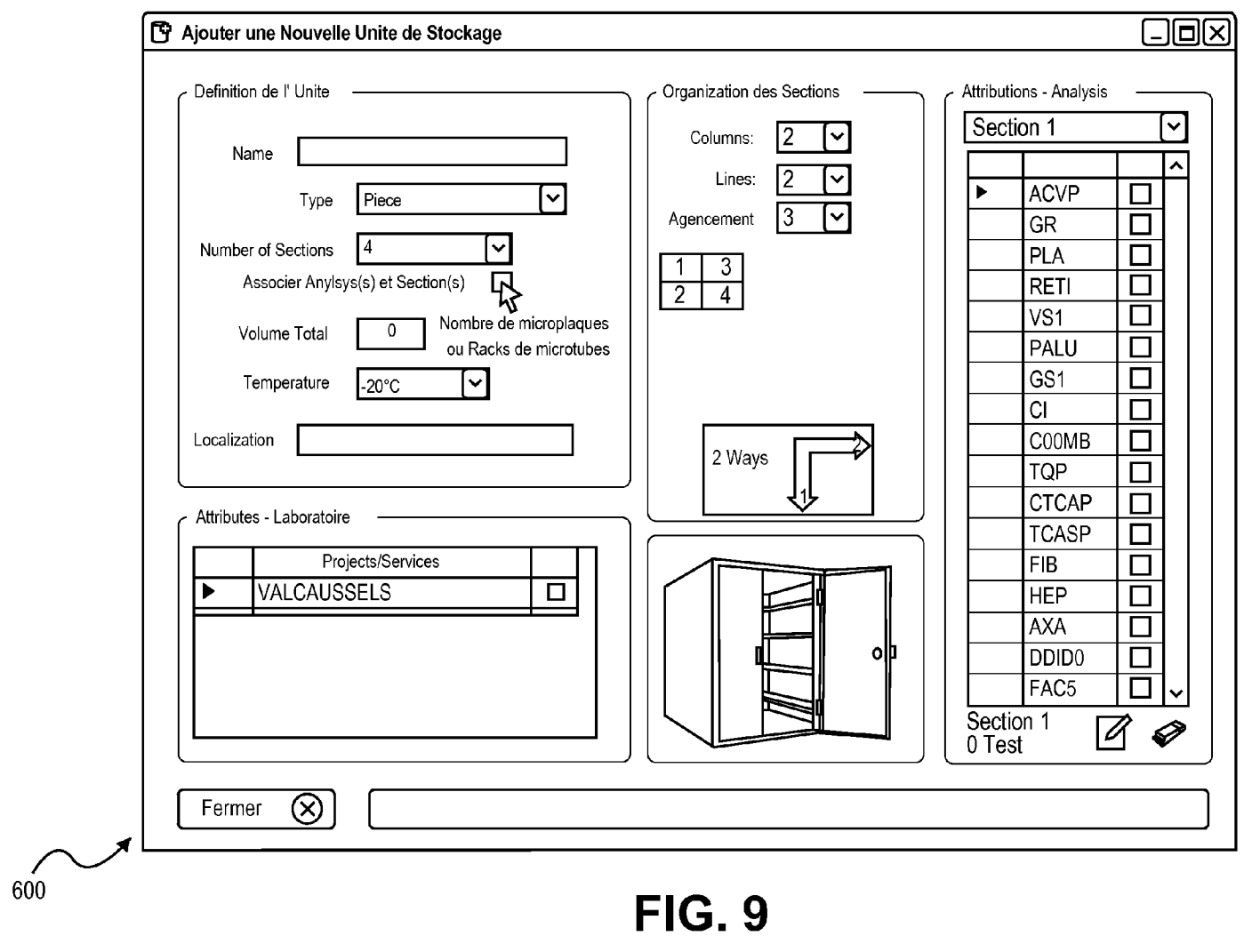

FIG. 9 shows a graphical user interface 600 which will allow a user to configure a specific storage unit. The test type, volume and number of sections in the storage unit can be specified using this graphical user interface 600. It is also possible to specify the number of sample containers or sample container holders, or the type of sample containers or sample container holders that can be placed in the storage unit. It is also possible to modify the system to specify which user has access to the storage unit.

Figure 10:
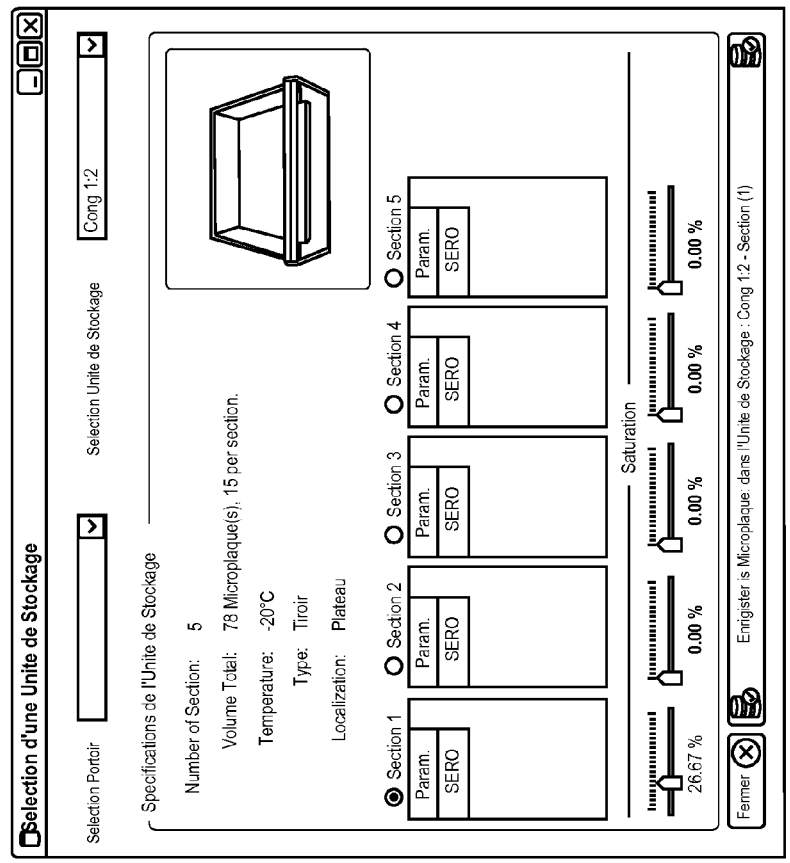
Figure 10:
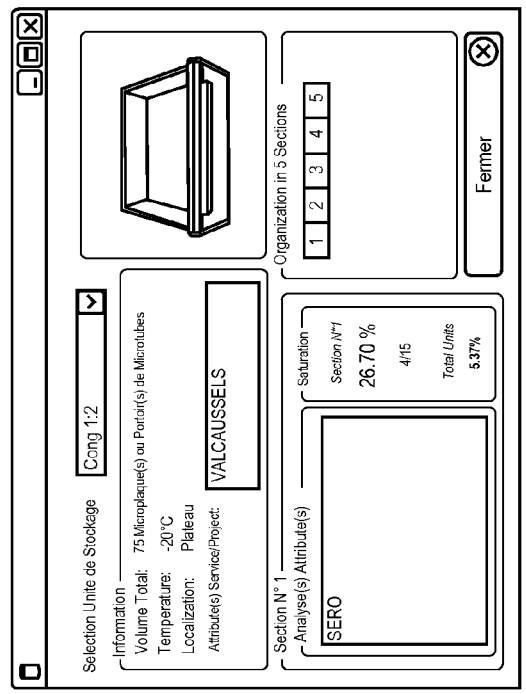

FIG. 10 shows a graphical user interface 700 which allows a user to configure drawers in a storage unit into sections. It is possible to determine how many sample containers or sample container holders, or the types of sample containers or sample container holders, that can be placed into each drawer. Thus, in embodiments of the invention, different drawers and sections within each drawer may also be configured by the user to store and hold sample containers or racks associated with a specific test type or other characteristic.

Figure 11:
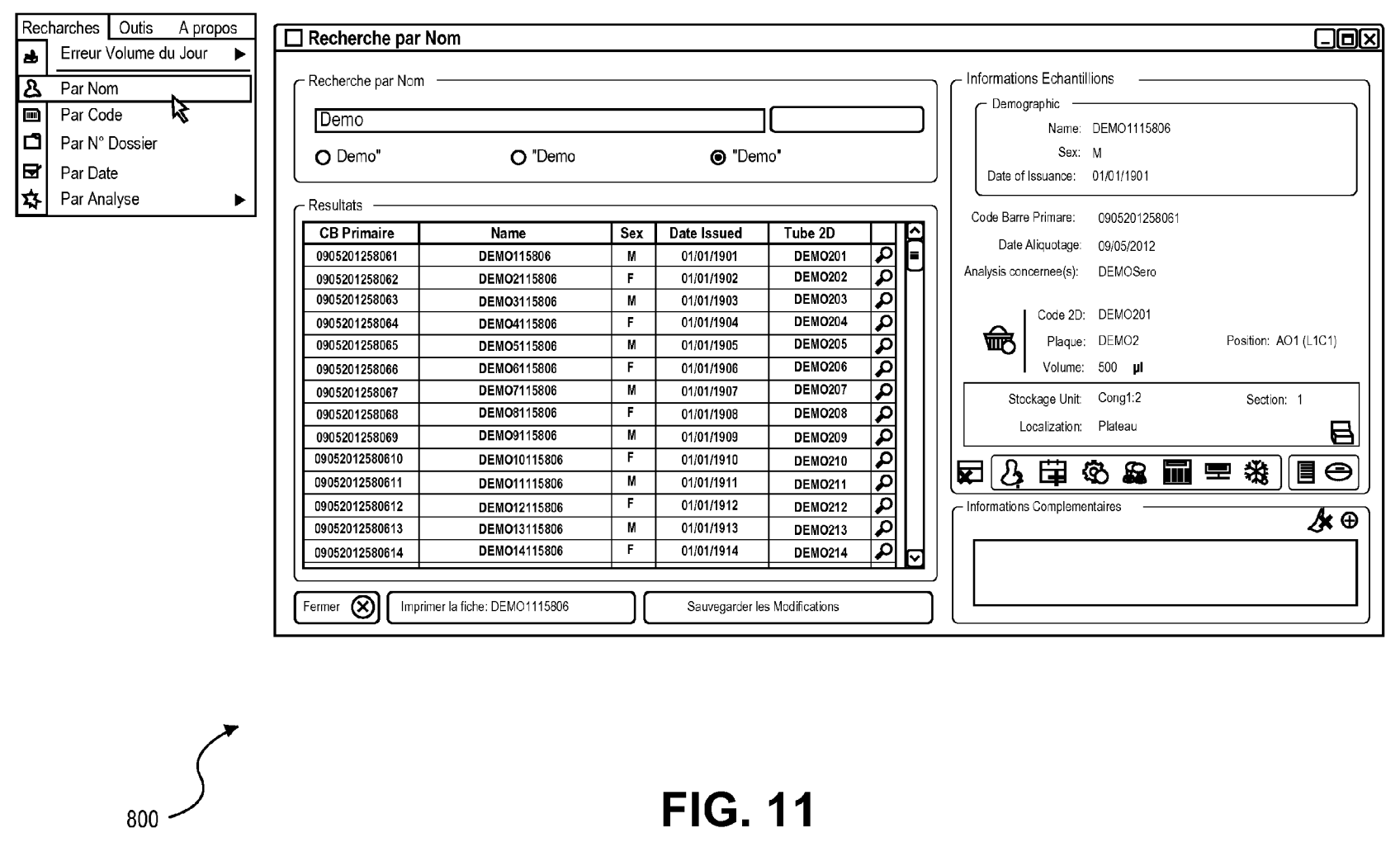

FIG. 11 shows a graphical user interface 800 which allows a user to retrieve samples by name, primary code, patient ID an aliquoting date. This can be used by a user to find out where a sample is stored in a storage unit.

Figure 12:
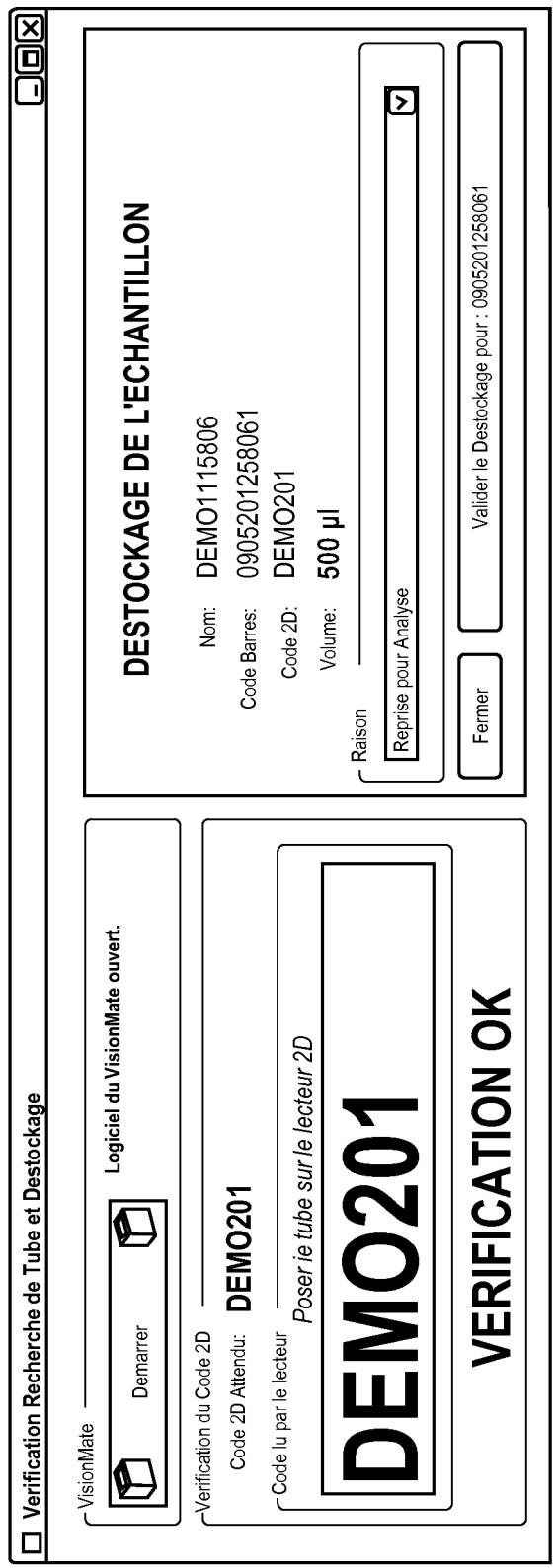

FIG. 12 shows a graphical user interface 900 that can be shown in a destocking process. Here it is possible to provide suggestions on which samples to destock (e.g., according to a time period).

Figure 13:
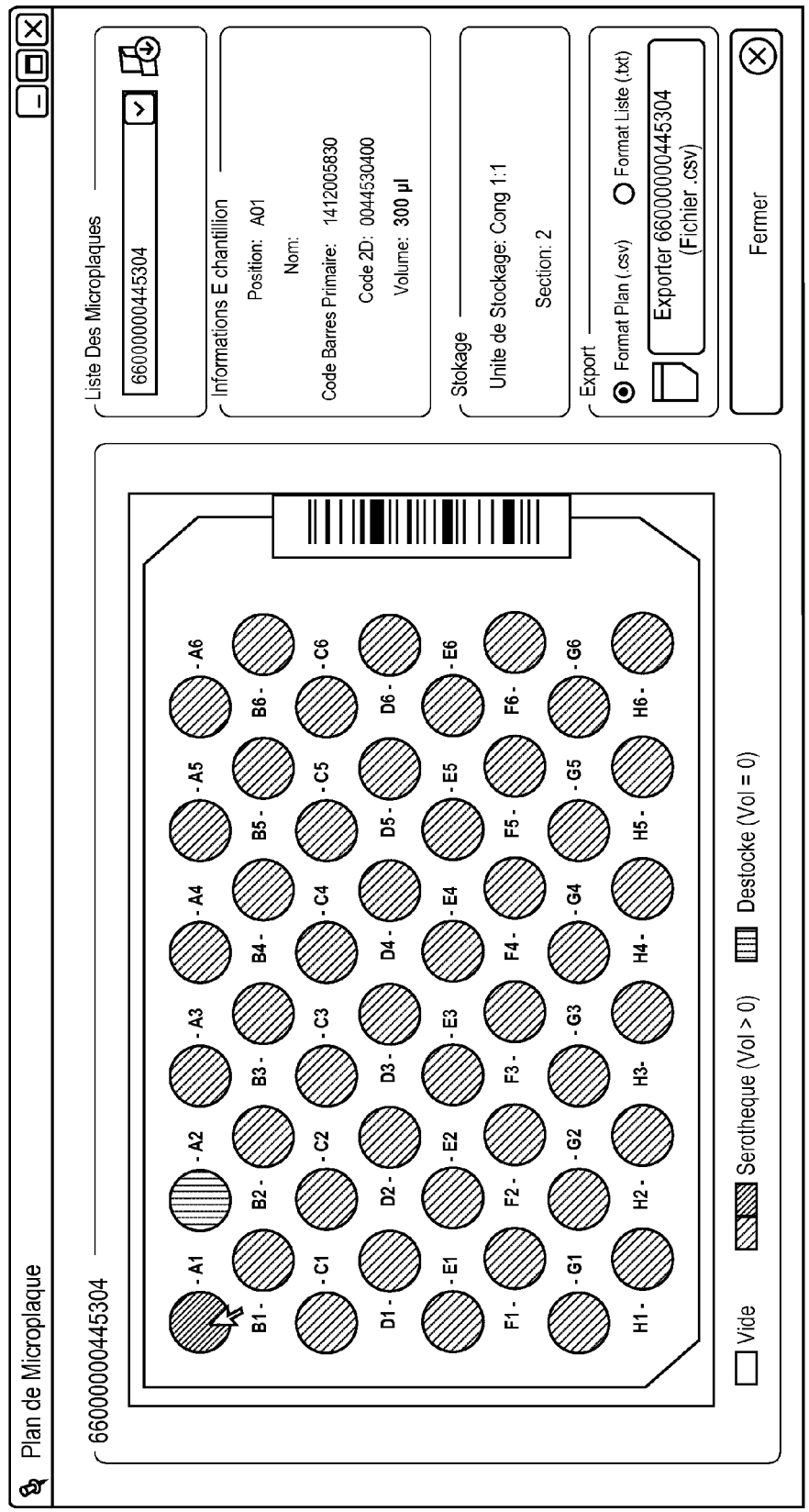

FIG. 13 shows a graphical user interface 1000 of a microtiter plate with different wells. A plate map for a microtiter plate is shown. For storage purposes, this can be used to identify the type of test associated with the microtiter plate.

Figure 14:
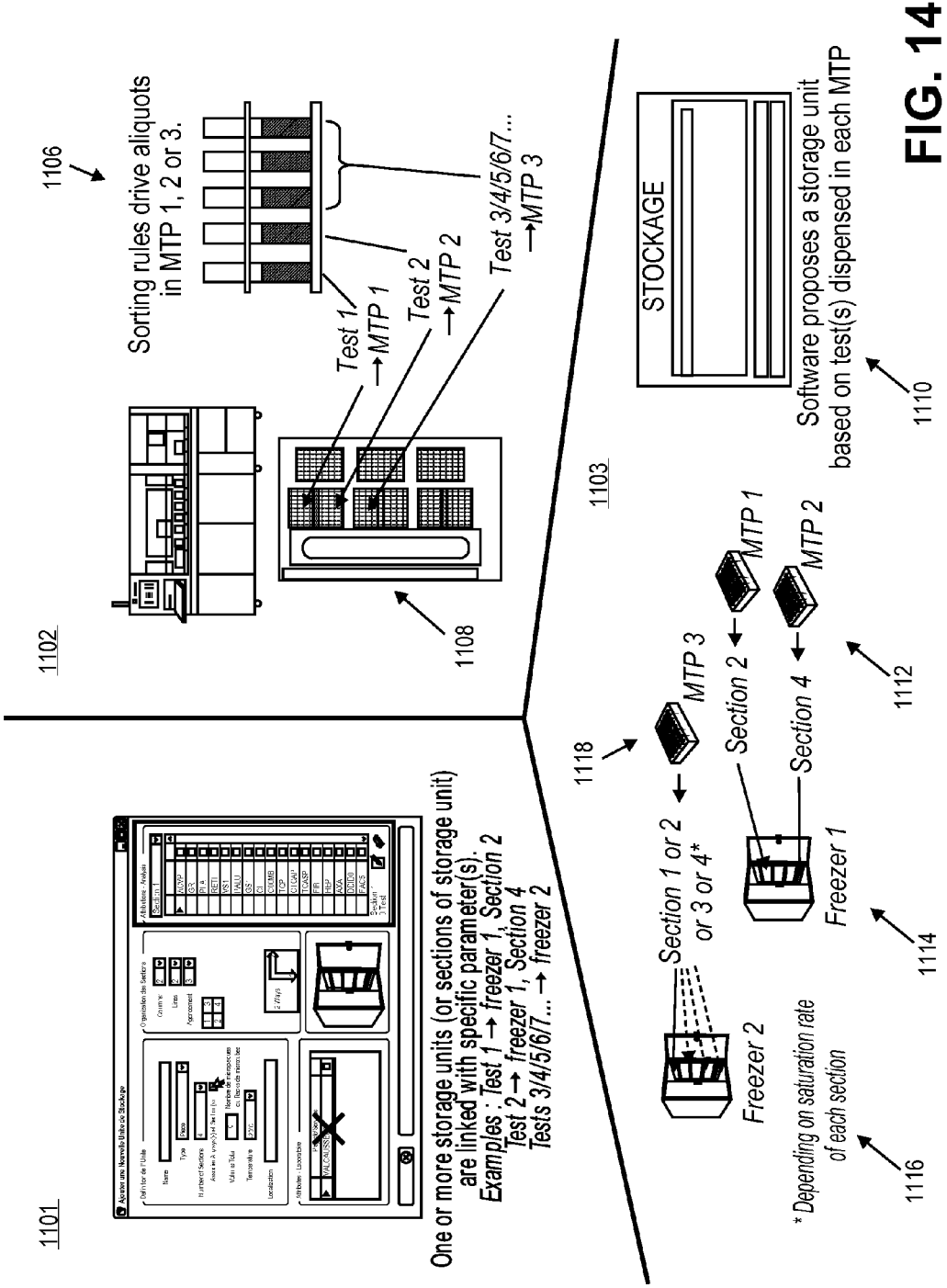
FIG. 14 shows a process flow according to an embodiment of the invention.

FIG. 14 shows a high level flow diagram of a multi serum bank configuration based on certain tests. Reference number 1101 designates a first step in the flow, and shows a graphical user interface which allows one or more storage units to be linked to specific parameters. For example, it is possible to store a first sample container comprising a first sample associated with Test 1 in freezer 1, section 2; a second sample container comprising a second sample associated with Test 2 in freezer 1, section 4, etc.

Reference number 1102, shows a second step in the flow. FIG. 14 shows a number of sample tubes 1106 with different tests associated with each sample tube. Samples are then provided to different multititer plates 1108 in an output drawer of a sample processing system. These samples may have been processed by the sample processing system.

Reference number 1103 shows a third step in the flow. Reference number 1103 shows a number of multititer plates 1112 that are provided to different regions in different storage units (e.g., freezer 1 and freezer 2) 1114, 1116. A user interface 1110 is also shown that proposes a storage unit and region within the storage unit based on the tests to be performed on the samples in the wells of each multititer plate.

It should be understood that the present invention as described above can be implemented in the form of control logic using computer software in a modular or integrated manner. Based on the disclosure and teachings provided herein, a person of ordinary skill in the art will know and appreciate other ways and/or methods to implement the present invention using hardware and a combination of hardware and software Any of the software components or functions described in this application, may be implemented as software code to be executed by a processor using any suitable computer language such as, for example, Java, C++ or Perl using, for example, conventional or object-oriented techniques. The software code may be stored as a series of instructions, or commands on a computer readable medium, such as a random access memory (RAM), a read only memory (ROM), a magnetic medium such as a hard-drive or a floppy disk, or an optical medium such as a CD-ROM. Any such computer readable medium may reside on or within a single computational apparatus, and may be present on or within different computational apparatuses within a system or network.

The above description is illustrative and is not restrictive. Many variations of the invention will become apparent to those skilled in the art upon review of the disclosure. The scope of the invention should, therefore, be determined not with reference to the above description, but instead should be determined with reference to the pending claims along with their full scope or equivalents.

One or more features from any embodiment may be combined with one or more features of any other embodiment without departing from the scope of the invention.

A recitation of "a", "an" or "the" is intended to mean "one or more" unless specifically indicated to the contrary.

What is claimed is:

1. A method for storing a sample container or a sample container holder in a storage unit comprising:
    identifying, by a processor, a sample container or a sample container holder associated with the sample container;
    accessing, by the processor, a location database storing mapping data correlating sample containers or sample container holders with sample containers to test regions in the storage unit, each test region corresponding to at least a portion of one or more shelves or drawers in the storage unit, wherein the test regions each store only one or more sample containers with samples that have been or are to be tested according to a particular test; and
    after accessing the database, providing, by the processor, a proposal for storage of the sample container or the sample container holder associated with the sample container in the storage unit.

2. The method of claim 1 wherein the storage unit is a refrigerator.

3. The method of claim 1 wherein each test region contains a plurality of locations.

4. The method of claim 1 wherein the storage unit comprises a number of sensors.

5. The method of claim 1 wherein the particular test is one of many different tests comprising an immunoassay test and a chemical test.

6. The method of claim 1 further comprising:
    processing a sample in the sample container in a sample processing system, prior to identifying the sample container.

7. The method of claim 1 wherein identifying the sample container or the sample container holder comprises identifying the sample container, and wherein providing the proposal for storage of the sample container or the sample container holder comprises providing the proposal for the sample container.

8. The method of claim 1 wherein a sensor is associated with each test region, the sensor configured to sense a presence or absence of the sample container or the sample container holder.

9. A central controller comprising:
    a processor; and
    a computer readable medium coupled to the processor, the computer readable medium comprising code, executable by the processor to implement a method comprising
    identifying, by a processor, a sample container or a sample container holder associated with the sample container,
    accessing, by the processor, a location database storing mapping data correlating sample containers or sample container holders with sample containers to test regions in the storage unit, each test region corresponding to at least a portion of one or more shelves or drawers in the storage unit, wherein the test regions each store only one or more sample containers with samples that have been or are to be tested according to a particular test, and
    after accessing the database, providing, by the processor, a proposal for storage of the sample container or the sample container holder associated with the sample container in the storage unit.

10. The central controller of claim 9 wherein the storage unit is a refrigerator.

11. The central controller of claim 9 wherein each test region contains a plurality of locations.

12. The central controller of claim 9 wherein the storage unit comprises a number of sensors.

13. The central controller of claim 9 wherein the particular test is one of many different tests comprising an immunoassay test and a chemical test.

14. The central controller of claim 9 wherein identifying the sample container or the sample container holder comprises identifying the sample container, and wherein providing the proposal for storage of the sample container or the sample container holder comprises providing the proposal for the sample container.

15. The central controller of claim 9 wherein a sensor is associated with each test region, the sensor configured to sense a presence or absence of the sample container or the sample container holder.

16. A system comprising:

a central controller comprising a processor, and a computer readable medium coupled to the processor, the computer readable medium comprising code, executable by the processor to implement a method comprising identifying, by a processor, a sample container or a sample container holder associated with the sample container, accessing, by the processor, a location database storing mapping data correlating sample containers or sample container holders with sample containers to test regions in the storage unit, each test region corresponding to at least a portion of one or more shelves or drawers in the storage unit, wherein the test regions each store only one or more sample containers with samples that have been or are to be tested according to a particular test, and after accessing the database, providing, by the processor, a proposal for storage of the sample container or the sample container holder associated with the sample container in the storage unit; and a sample container holder location database coupled to the central controller.

17. The system of claim 16 further comprising a sample processing system coupled to the central controller.

18. The system of claim 16 further comprising a storage unit coupled to the central controller.

19. The system of claim 16 further comprising a scanning device coupled to the central controller.

20. The system of claim 16 further comprising a sample processing system, a storage unit, and a scanner coupled to the central controller.

* * * * *